(12) United States Patent  
Nielsen et al.

(10) Patent No.: US 7,680,608 B2
(45) Date of Patent: Mar. 16, 2010

(54) METHOD OF DETERMINING A SPATIAL DISTRIBUTION OF MAGNETIC PARTICLES

(75) Inventors: Tim Nielsen, Hamburg (DE); Bernhard Gleich, Hamburg (NL); Jurgen Weizenecker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 442 days.

(21) Appl. No.: 11/721,062

(22) PCT Filed: Dec. 5, 2005

(86) PCT No.: PCT/IB2005/054042

§ 371 (c)(1), (2), (4) Date: Jun. 7, 2007

(87) PCT Pub. No.: WO2006/064392

PCT Pub. Date: Jun. 22, 2006

(65) Prior Publication Data

US 2009/0234588 A1   Sep. 17, 2009

(30) Foreign Application Priority Data

Dec. 14, 2004  (EP) .................................. 04106541

(51) Int. Cl.
*G01N 31/00*  (2006.01)
*G01C 25/00*  (2006.01)

(52) U.S. Cl. .................... 702/23; 702/115; 702/116; 702/117

(58) Field of Classification Search ............. 702/23–29, 702/38, 115–118; 324/765

See application file for complete search history.

(56) References Cited

U.S. PATENT DOCUMENTS 5,111,141 A * 5/1992 Fukuhara et al. ............. 324/250
7,246,939 B1 * 7/2007 Gultekin ...................... 374/44

FOREIGN PATENT DOCUMENTS

DE   10151778 A1   5/2003

* cited by examiner

*Primary Examiner*—Eliseo Ramos Feliciano
*Assistant Examiner*—Phuong Huynh (57) ABSTRACT

The invention relates to a method of determining a spatial distribution of magnetic particles in an examination area, in which a magnetic field is generated which has a first part-region having a relatively low magnetic field strength and a second part-region having a relatively high magnetic field strength. The position of the two part-regions is changed, as a result of which the magnetization in the examination area changes, and real measured values which depend on the change in magnetization are recorded. A dependence distribution which depends on a spatial distribution of magnetic particles is then determined such that a sum which comprises as summands a) the difference of the real measured values from fictitious measured values which are determined by applying a transfer function to the dependence distribution, and b) the product of a regularization parameter and of a regularization value which is determined by applying the regularization functional to the dependence distribution, is minimized. Finally, the spatial distribution of magnetic particles is determined by means of the determined dependence distribution.

13 Claims, 4 Drawing Sheets

METHOD OF DETERMINING A SPATIAL DISTRIBUTION OF MAGNETIC PARTICLES

The invention relates to a method of determining a spatial distribution of magnetic particles in an examination area. The invention furthermore relates to an apparatus for carrying out the method according to the invention and to a computer program for controlling the apparatus according to the invention.

A method of the type mentioned above is known from DE 101 51 778. In the method described in said document, firstly a magnetic field is generated such that in the examination area there is a first part-region having a relatively low magnetic field strength and a second part-region having a relatively high magnetic field strength, that is to say in the first part-region the magnetic field strength is lower than in the second part-region. The spatial position of the part-regions in the examination area is then changed so that the magnetization of the particles in the examination area changes locally. Signals are recorded which depend on the magnetization in the examination area, said magnetization being influenced by the change in spatial position of the part-regions, wherein information regarding the spatial distribution of the magnetic particles in the examination area is obtained from these signals so that an image of the examination area can be produced. DE 101 51 778 proposes reconstructing an image of the examination area by applying to the measured signals a reconvolution operation with a magnetization function which depends on the magnetization characteristic of the magnetic particles.

One disadvantage of this known method is that the reconstruction leads to images of the examination area which have a quality that is often not sufficient for example for a diagnosis in medical applications.

It is therefore an object of the present invention to provide a method of the type mentioned above in which the quality of the produced image is improved.

This object is achieved by a method of determining a spatial distribution of magnetic particles in an examination area, comprising the steps a) generating a first, temporally constant magnetic field with a spatial course of the magnetic field strength such that in the examination area there is a first part-region having a relatively low magnetic field strength and a second part-region having a relatively high magnetic field strength, b) changing the spatial position of the two part-regions in the examination area so that the magnetization of the particles changes locally, c) recording real measured values which depend on the magnetization in the examination area, said magnetization being influenced by the change in position of the two part-regions, d) reconstructing the spatial distribution of magnetic particles in the examination area from the real measured values, by means of the following steps:

providing a transfer function which, applied to a dependence distribution which depends on a spatial distribution of magnetic particles, supplies fictitious measured values, and also providing a regularization parameter and a regularization functional which can be applied to a dependence distribution which depends on a spatial distribution of magnetic particles, determining a dependence distribution which depends on a spatial distribution of magnetic particles, such that a sum which comprises as summands i) the difference of the real measured values from fictitious measured values which are determined by applying the transfer function to the dependence distribution, and ii) the product of the regularization parameter and of a regularization value which is determined by applying the regularization functional to the dependence distribution, is minimized, e) determining the spatial distribution of magnetic particles from the determined dependence distribution.

The expression "real measured values" includes measured values which have been recorded in step c) or which have been determined directly from these recorded measured values, for example by means of a Fourier transformation or by multiplication by a factor. By contrast, the expression "fictitious measured values" refers to measured values which are determined by applying the transfer function to a dependence distribution.

The dependence distribution is dependent on the spatial distribution of magnetic particles and thus contains information about this spatial distribution of magnetic particles, so that this spatial distribution can be determined in step e).

According to the invention, therefore, a transfer function which, applied to a dependence distribution which is for example the same as the spatial distribution of magnetic particles, leads to fictitious measured values is provided, along with a regularization parameter and a regularization functional. The use of the transfer function, the regularization parameter and the regularization functional according to step d) leads to an image quality of the spatial distribution of magnetic particles in the examination area which is improved compared to the image quality in the method described in DE 101 51 778.

The dependence distribution is the same as the distribution of magnetic particles in the examination area, and as a result step e) can be omitted and the method according to the invention is simplified.

In the embodiment, a transfer function is determined and provided in a manner which is easy to carry out and with a low calculation complexity.

A spatial test distribution of magnetic particles in the examination area is provided and in each case spatial distributions of magnetic particles are calculated for different combinations of regularization parameter and regularization functional. In step d), that combination of regularization parameter and regularization functional is then provided for which the difference of the calculated spatial distribution from the spatial test distribution is smallest. This procedure leads to reconstructed images of further improved quality.

The transfer function is represented as the transfer matrix and a singular value decomposition is applied to the transfer matrix. By virtue of the singular value decomposition, the transfer matrix is decomposed into a first matrix, a diagonal matrix and a second matrix. If the spatial test distribution is reconstructed a number of times using different combinations of regularization parameter and regularization functional, the same first matrix, the same diagonal matrix and the same second matrix are used for each of these reconstructions. The diagonal matrix can be inverted easily, that is to say with a low calculation complexity. In particular, the calculation complexity is lower than the calculation complexity for inverting the transfer matrix. This ability to be easily inverted usually leads, as explained in more detail below, to a lower calculation complexity when reconstructing the spatial test distribution for a combination of regularization parameter and regularization functional, as a result of which the calculation complexity for providing the regularization parameter and the regularization functional in step d) is further reduced.

An improved image quality compared to the prior art is also achieved if the regularization parameter is equal to zero, wherein such an embodiment has the advantage that the calculation complexity for reconstructing an image of the spatial distribution of magnetic particles is reduced.

Prior to the reconstruction in step d), the real measured values recorded in step c) are transformed, in particular by means of a Fourier transformation, in such a manner that the number of transformed real measured values is smaller than the number of real measured values recorded in step c). This is useful for example when the recorded real measured values have only a certain bandwidth, e.g. on account of filter properties of the measurement system, so that, following a Fourier transformation, some Fourier-transformed real measured values are so small that they cannot be distinguished from the noise of the measurement system and can be omitted in the following steps according to the invention. The transformation preferably comprises a Fourier transformation of the real measured values and a subsequent omission of Fourier-transformed real measured values which are so small that they cannot be distinguished from the noise of the measurement system. Such a reduction in the number of measured values leads to a further reduction in the calculation complexity during the reconstruction in step d).

It is also described the recorded measured values may be transformed in such a manner that in step d) a transfer function can be provided which is easier to invert, i.e. with a lower calculation complexity, than a transfer function which would be provided if the measured values were not transformed. One transfer function can be inverted with a lower calculation complexity than another transfer function if a computer requires less time for inverting one transfer function than for inverting the other transfer function. The transformation of the measured values affects the appearance of the transfer matrix since the transfer matrix describes how measured values are generated from the spatial distribution of magnetic particles which exists in the examination area. The transfer matrix thus depends directly on the representation of the recorded real measured values, so that, by suitably selecting the transformation of the measured values, in step d) a transfer matrix can be provided which is more easily inverted, for example since it comprises more non-diagonal elements which are equal to zero than a transfer matrix which can be provided if the measured values are not transformed. As a result, as will be explained in more detail below, the calculation complexity is further reduced.

When use is made of transformed real measured values, a transfer function can be determined and provided in a manner which is easy to carry out and with a low calculation complexity.

A method by means of which the sum can be minimized with a low calculation complexity.

Firstly, a preliminary transfer matrix is provided. Then, a product matrix is formed from this preliminary matrix and a transformation matrix, wherein the transformation matrix is designed in such a way that the product matrix can be more easily inverted than the preliminary transfer matrix, i.e. with a lower calculation complexity, since it comprises for example more non-diagonal elements which are equal to zero. In the subsequent reconstruction, the more easily invertible product matrix is then provided as the transfer matrix, and this leads to a further reduction in the calculation complexity.

In the embodiment, the preliminary transfer function is determined and provided in a manner which is easy to carry out and with a low calculation complexity.

An apparatus for carrying out the method according to the invention and a computer program for controlling an apparatus are discribed.

The invention will be further described with reference to examples of embodiments shown in the drawings to which, however, the invention is not restricted.

Figure 1:
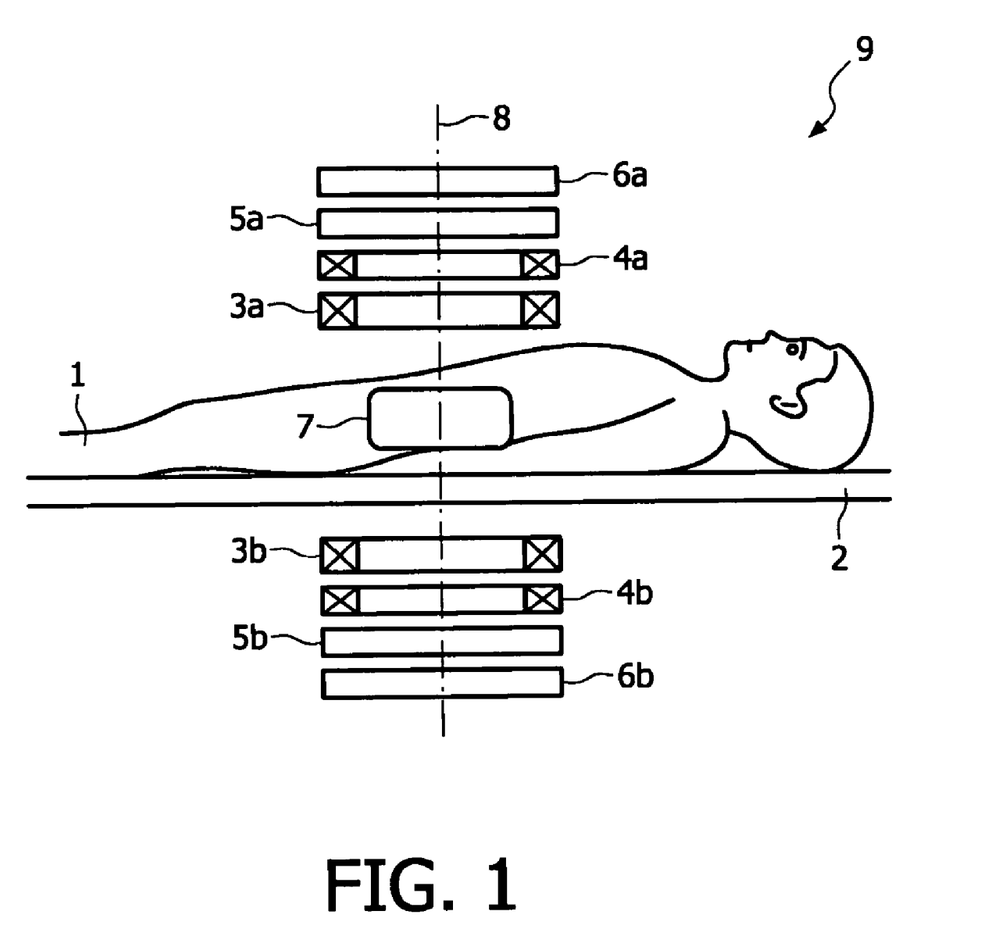
FIG. 1 shows a schematic diagram of an apparatus according to the invention for carrying out the method according to the invention.

FIG. 1 shows one embodiment of an apparatus 9 according to the invention. An object, in this case a patient 1, is located on a patient table 2. Inside the patient 1, for example in the gastrointestinal tract, and in an examination area of the apparatus 9 there are magnetic particles which have been administered to the patient for example in a liquid or semisolid form. As will be explained in more detail below, the size of the examination area depends in particular on the magnetic fields and magnetic particles used.

Figure 2:
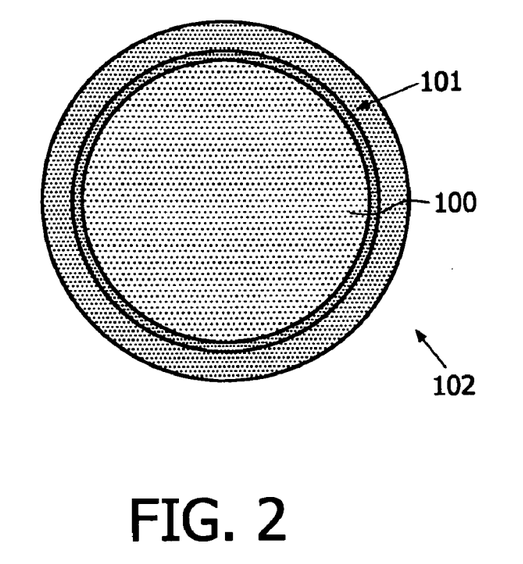
FIG. 2 shows one of the magnetic particles present in the examination area.

One magnetic particle is shown in FIG. 2. It comprises a spherical substrate 100, for example made of glass, which is coated with an e.g. 5 nm-thick soft-magnetic layer 101 which consists for example of an iron-nickel alloy (e.g. Permalloy). This layer may be covered for example by a top layer 102 which protects the particles against acid. The strength of the magnetic field which is required to saturate the magnetization of such particles depends on the diameter of the latter. To this end, a magnetic field of 1 mT is required for a diameter of 10 μm whereas a magnetic field of 100 μT is sufficient for a diameter of 100 μm. If a coating having a lower saturation magnetization than Permalloy is selected, the magnetic field which is required for saturation is of course further reduced.

For the sake of simplicity, the magnetic field strengths mentioned within the context of the invention are given in Tesla. This is not quite correct since Tesla is the unit for magnetic flux density. In order to obtain the respective magnetic field strength, the value specified in each case must be divided by the magnetic field constant $\mu_0$.

The invention is not restricted to the magnetic particle just described. Rather, the method according to the invention can be carried out using any magnetic particle which has a non-linear magnetization characteristic, that is to say in which the course of the magnetization of the magnetic particle as a function of a magnetic field strength acting on the particle is non-linear.

Use may also be made of so-called monodomain particles of ferromagnetic or ferrimagnetic material. These particles have dimensions in the nanometer range and are so small that no magnetic domains or Weiss' domains can form therein. These particles may be injected into a patient's bloodstream in a suitable colloidal dispersion. Such dispersions are already injected as contrast agents in the magnetic resonance sector (MR sector). The magnetic particles used there have a size of 5 to 10 nm. However, this size is not optimal for the method according to the invention since the magnetic field strength required for saturation decreases with the third power of the particle diameter. The magnetic particles should therefore be as large as possible but not so large that magnetic domains can form. Depending on the magnetic material, the optimal size of a magnetic monodomain particle lies between 20 and 800 nm. One material suitable for monodomain particles is for example magnetite ($Fe_3O_4$). Such particles can be inhaled for example for lung examinations.

Within the context of the invention, the expression "magnetic particles" also comprises particles which can be magnetized.

Located above and below the patient 1 is a first coil pair 3a, 3b (first magnetic means) which comprises two identical coils 3a, 3b arranged coaxially above and below the patient 1 (cf. FIG. 1), which coils are flowed through by currents of identical magnitude but in opposite directions and generate a first, temporally constant magnetic field. The first magnetic field is shown by the field lines 300 in FIG. 3. In the direction of the common coil axis 8, it has an almost constant gradient, wherein it reaches a zero value at one point on this coil axis. Starting from this field-free point, the magnetic field strength increases in all spatial directions as the distance from the field-free point increases. In a first part-region 301, which is shown in dashed line in FIG. 3 and is arranged around the field-free point, the magnetic field strength of the first magnetic field is so low that the magnetization of magnetic particles located there is not saturated. In a second part-region 302 on the other hand, which lies outside the first part-region 301, the magnetization of the magnetic particles is saturated.

Figure 3:
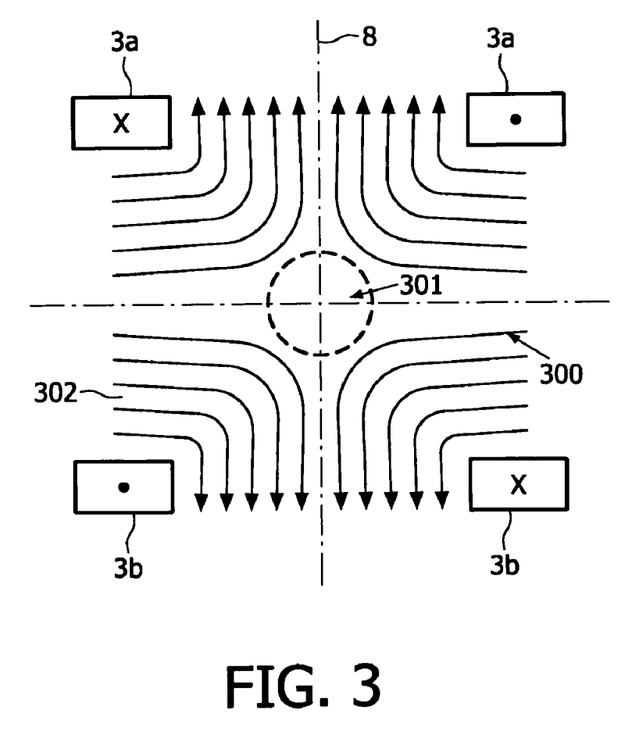
FIG. 3 shows a field line course of a first, temporally constant magnetic field in the apparatus of FIG. 1.

The first part-region 301 of the first magnetic field can be shifted in the examination area by means of a second, temporally variable magnetic field which is superposed on the first magnetic field.

The movement and dimensions of the first part-region 301, the magnetic properties and the distribution of the magnetic particles determine the size of the examination area. The examination area covers every area of the object to be examined, i.e. of the patient 1 for example, which has magnetic particles the magnetization of which is changed on account of the change in position of the first part-region 301.

Three further coil pairs (second magnetic means) are provided for generating the second, temporally variable magnetic field. The coil pair 4a, 4b generates a magnetic field component of the second magnetic field which runs in the direction of the coil axis 8 of the first coil pair 3a, 3b. For this purpose, the coils 4a, 4b are flowed through in the same direction by currents of identical magnitude. In principle, the effect which can be achieved by the coil pair 4a, 4b can also be achieved by superposing currents of the same direction on the identical currents of opposite direction in the first coil pair 3a, 3b, as a result of which the current decreases in one coil pair and increases in the other coil pair.

In order to generate magnetic field components of the second magnetic field in directions oriented perpendicular to the coil axis of the coil pair 3a, 3b, use is made of two further coil pairs 5a, 5b and 6a, 6b. These coil pairs 5a, 5b and 6a, 6b, like the coil pairs 3a, 3b and 4a, 4b, could be of the Helmholtz type, but then the examination area would be surrounded by the coil pairs in all three spatial directions and as a result access to the examination area would be made more difficult. The coils 5a, 6a are therefore arranged above the patient 1 and the coils 5b, 6b are arranged below the patient 1. The coils 5a, 5b generate a magnetic field component the direction of which is oriented perpendicular to the coil axis 8. Moreover, the coils 6a, 6b generate a magnetic field component the direction of which is oriented perpendicular to the coil axis 8 and perpendicular to the direction of the magnetic field component generated by the coil pair 5a, 5b. The coils 5a, 5b, 6a, 6b therefore generate magnetic field components which are oriented perpendicular to their coil axis. Such coils are not of the Helmholtz type and are known from magnetic resonance devices with open magnets ("open MRI"), in which a high-frequency coil pair which can generate a horizontal, temporally variable magnetic field is located above and below the patient. The design of these known coils 5a, 5b, 6a, 6b will not be discussed in any greater detail here.

The coil pairs 4a, 4b . . . 6a, 6b therefore generate the temporally variable, second magnetic field, by means of which the first part-region 301 of the first magnetic field can be moved in the examination area, which in this case is three-dimensional but may alternatively also be one-dimensional or two-dimensional. The movement of the first part-region 301 in the examination area leads to a change in the magnetization of the magnetic particles 102, as a result of which signals are induced in a suitable receiving coil. The relationship between the movement of the first part-region 301 and the changing magnetization of the magnetic particles and the resulting induced signals is discussed in more detail in DE 101 51 778, to which reference is hereby made.

FIG. 1 schematically shows a receiving coil 7 (recording means) which is adapted such that signals (real measured values) can be induced in the receiving coil 7 on account of a changing magnetization in the examination area. In principle, any of the field-generating coil pairs 3a, 3b . . . 6a, 6b could also be used for this purpose. One or more separate receiving coils 7 nevertheless have the advantage that they can be arranged and switched independently of the field-generating coils 3a, 3b . . . 6a, 6b and lead to an improved signal-to-noise ratio. The induction of signals in the receiving coil 7 on account of the change in magnetization of the magnetic particles 102 is described in more detail in DE 101 51 778.

If the change in magnetization is to be detected in all three spatial directions, at least one receiving coil is required for each spatial direction, which receiving coil can receive the corresponding directional component of the change in magnetization.

Figure 4:
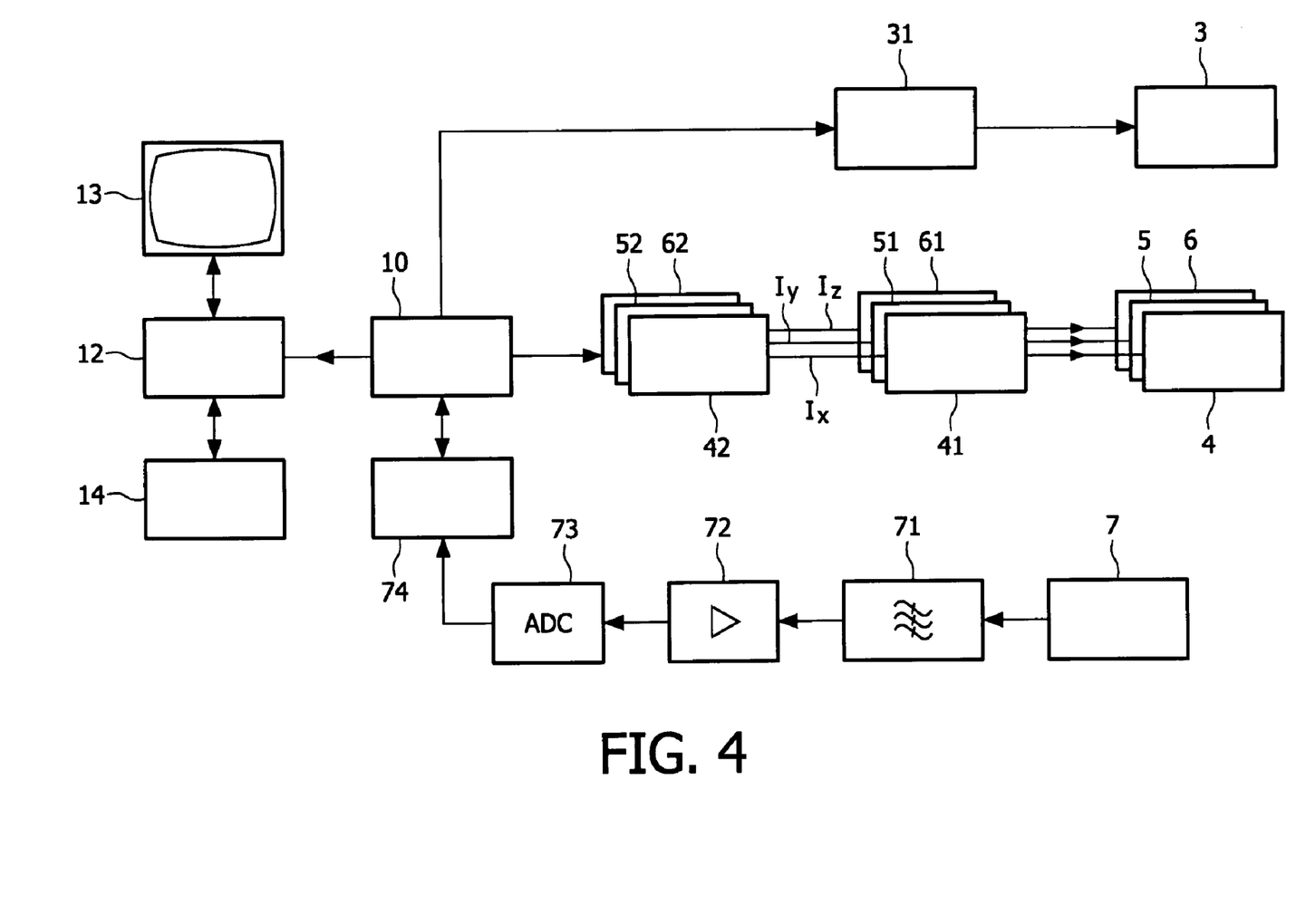
FIG. 4 shows a block diagram of the apparatus of FIG. 1.

FIG. 4 shows a block diagram of the apparatus 9 shown in FIG. 1. The coil pair 3a, 3b is shown schematically in FIG. 4 and bears the reference 3 for the sake of clarity. The same applies in respect of the coil pairs 4a, 4b . . . 6a, 6b.

The coil pair (first magnetic means) 3 is supplied with a DC current from a controllable current source 31, said current source being controlled by the control unit 10. The control unit 10 is connected to a computer 12 which comprises a monitor 13 for displaying the distribution of magnetic particles in the examination area and an input unit 14, for example a keyboard 14.

The coil pairs (second magnetic means) 4, 5, 6 are connected to current amplifiers 41, 51, 61, from which they receive their currents. The current amplifiers 41, 51, 61 are in turn in each case connected to an AC current source 42, 52, 62 which defines the temporal course of the currents $I_x, I_y, I_z$ to be amplified. The AC current sources 42, 52, 62 are controlled by the control unit 10.

The receiving coil (recording means) 7 is also shown schematically in FIG. 4. The signals induced in the receiving coil 7 are fed to a filter unit 71, by means of which the signals are filtered. The aim of this filtering is to separate measured values, which are caused by the magnetization in the examination area which is influenced by the change in position of the two part-regions (301, 302), from other, interfering signals. To this end, the filter unit 71 may be designed for example such that signals which have temporal frequencies that are smaller than the temporal frequencies with which the coil pairs 4, 5, 6 are operated, or smaller than twice these temporal frequencies, do not pass the filter unit 71. The signals are then transmitted via an amplifier unit 72 to an analog/digital converter 73 (ADC). The digitalized signals produced by the analog/digital converter 73 are fed to an image processing unit (reconstruction means) 74, which reconstructs the spatial distribution of the magnetic particles from these signals and the respective position which the first part-region 301 of the first magnetic field in the examination area assumed during receipt of the respective signal and which the image processing unit 74 obtains from the control unit 10. The reconstructed spatial distribution of the magnetic particles is finally transmitted via the control unit 10 to the computer 12, which displays it on the monitor 13.

Figure 5:
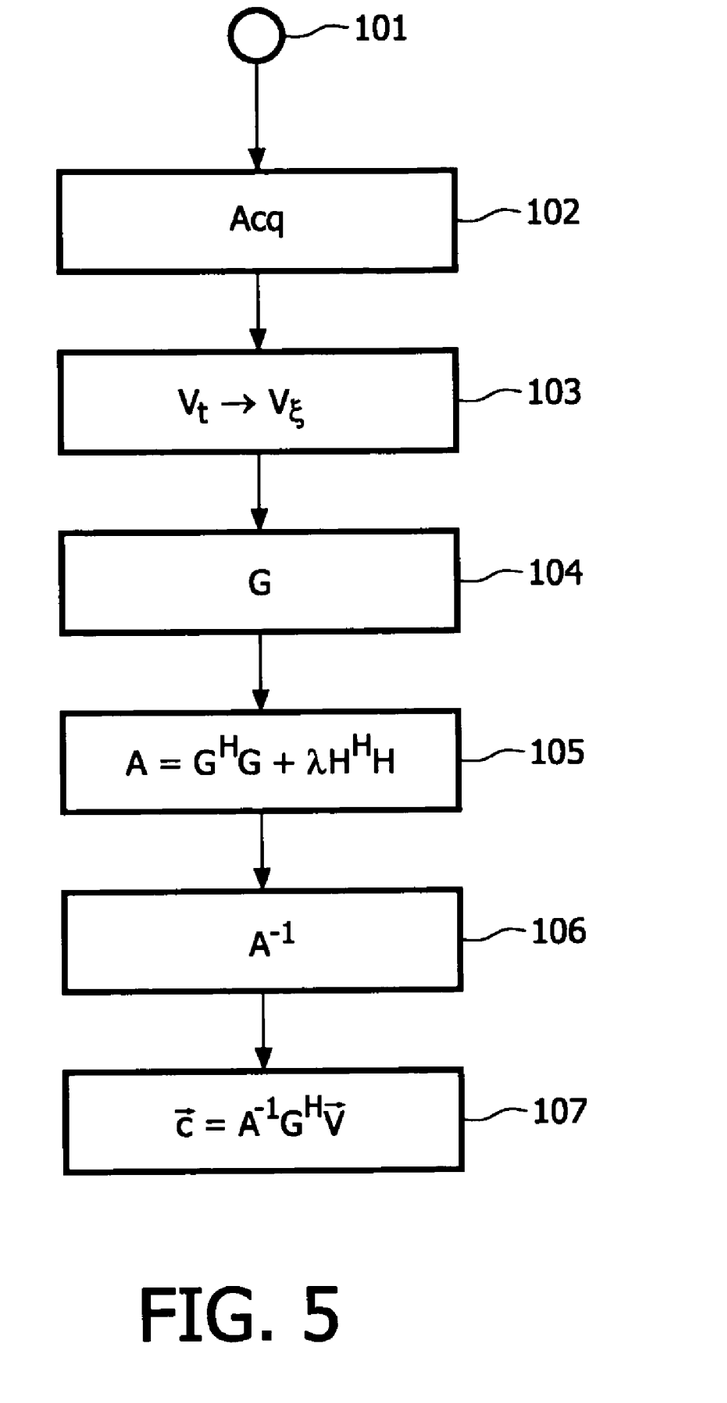
FIG. 5 shows a flow chart of a method according to the invention.

FIG. 5 shows the progress of a method according to the invention which can be carried out using the apparatus as shown in FIG. 1.

Following the initialization in step 101, the coils 3a, 3b generate the first magnetic field comprising the two part-regions 301 and 302.

In step 102, the position of the two part-regions 301 and 302 in the examination area is changed by the temporally variable, second magnetic field. The second magnetic field is configured such that the first part-region 301 moves along a path in the examination area, which is designed such that the entire examination area is covered by the first part-region 301. By virtue of the movement of the two part-regions 301 and 302 in the examination area, the magnetization of magnetic particles in the examination area changes. Prior to the method being carried out, these magnetic particles have been introduced into the examination area for example by a patient ingesting magnetic particles in semisolid form for the purpose of examining the gastrointestinal tract. The changing magnetization of the magnetic particles in the examination area leads to induced signals in the receiving coil 7, that is to say to real measured values which are measured by the above-described apparatus 9.

Alternatively, the change in spatial position of the two part-regions 301 and 302 in the examination area could also be brought about without the second magnetic field, by moving the examination area for example by moving the patient table 2 on which the patient 1 is located. Furthermore, the examination area and the two part-regions 301 and 302 could also be moved simultaneously on account of the second magnetic field. It is important that the position of the two part-regions 301 and 302 changes relative to the examination area.

In step 102, the signals are measured continuously over time. In step 103, these signals or real measured values $V_t$, which are thus time-dependent, are transformed in a so-called evaluation space, which in this case is a frequency space, that is to say the recorded measured values $V_t$ are Fourier-transformed and then those Fourier-transformed real measured values which are so small that they cannot be distinguished from the noise of the measurement system are omitted. In the frequency space, the transformed measured values are denoted $V_\xi$, that is to say $V_t$ denotes a measured value recorded at the time t and $V_\xi$ denotes a transformed measured value having the frequency $\omega_\xi$. The times t and frequencies $\omega_\xi$ are referred to as index values, wherein an index value is assigned to each measured value. Each recorded measured value $V_t$ is assigned a time t as an index value, and each transformed measured value $V_\xi$ is assigned a frequency $\omega_\xi$ as an index value.

By virtue of the transformation in the evaluation space, the calculation and storage complexity in the following steps 104 to 105 is reduced. The apparatus 9 according to the invention has filter properties on account of the electrical components used. Furthermore, the bandwidth of recorded real measured values is limited by the properties of the magnetic particles, for example by their size. There are therefore fewer transformed real measured values $V_\xi$, that is to say Fourier-transformed measured values, which are so large that they can be distinguished from the noise of the measurement system than there are non-transformed real measured values $V_t$, so that the calculation complexity is reduced in the following steps in which the transformed real measured values are used. By virtue of such a procedure, real measured values which do not help to improve the image quality are not taken into account in the reconstruction.

If the filter properties of the overall system, that is to say the filter properties which are determined by the apparatus 9 according to the invention and by properties of the magnetic particles, are known, for example from measurements which have already been carried out, in other embodiments the limited bandwidth of the recorded real measured values could be taken into account by not taking account of certain real measured values $V_t$ in the following steps, without a Fourier transformation being carried out. If, for example, the highest measured frequency can be detected with a temporal sampling rate (measured signals per unit time) which is only half as great as the sampling rate used during the acquisition in step 102, in each case two temporally adjacent real measured values may be replaced by their mean value. Alternatively, it is also possible for only every second measured real measured value to be taken into account in the following steps.

Alternatively, use may be made of any transformation, in particular of any linear transformation, which transforms the recorded real measured values in an evaluation space in such a way that the calculation complexity in steps 104 to 107 is reduced. This may be effected for example, as described above, by using a transformation which produces transformed real measured values the number of which is smaller than the number of non-transformed real measured values and the use of which in steps 104 to 107 does not lead to a reduction in image quality. Use may furthermore be made of a transformation which leads to a transfer function being provided which describes the relationship between the existing distribution of magnetic particles and the transformed real measured values and which leads to the intermediate matrix A described below being more easily inverted than an intermediate matrix A which would exist if the transfer function were to describe the relationship between the existing distribution of magnetic particles and the non-transformed real measured values. A matrix can be more easily inverted than another matrix for example when the calculation complexity of the inversion for one matrix is lower than for the other matrix. This easier invertability of the intermediate matrix A exists for example when the regularization matrix described below is unitary and when the real measured values are transformed in such a manner that the transfer matrix comprises as many non-diagonal elements as possible which are equal to zero.

In step 104, a transfer matrix $G_{\xi,i}$ is determined for the transformed measured values $V_\xi$. The transfer matrix $G_{\xi,i}$ describes the relationship between the distribution $c_i$ of magnetic particles which exists in the examination area and the transformed real measured values $V_\xi$, wherein $c_i$ is the concentration of magnetic particles at the location $\vec{x}_i$ in the examination area:

$$V_\xi = G_{\xi,i} c_i \qquad (1)$$

In order to determine the transfer matrix $G_{\xi,i}$ the magnetic particles are removed from the examination area and a delta probe is successively positioned at all locations $\vec{x}_i$, in the examination area. A delta probe is a quantity of magnetic particles which is restricted to a spatial area which is as narrow as possible but which is nevertheless large enough that a signal which can be measured and evaluated is induced in the receiving coil in the event of a change in the second magnetic field.

When the delta probe is positioned at a specific location $\vec{x}_k$, the part-regions 301 and 302 are moved relative to the examination area, in this case by the second magnetic field, in the same way as during the measurement in step 102. The signals induced in the receiving coil, that is to say the real measured values, are measured and transformed in the evaluation space as in step 103.

The delta probe can be described by $$c_i = \delta_{i,k} c_k \qquad (2)$$

where $$\delta_{i,k} = \begin{cases} 1 & \text{for } i = k \\ 0 & \text{otherwise} \end{cases}$$

wherein $c_k$ is the concentration of magnetic particles at the location $\vec{x}_k$ when the delta probe is arranged at this position. When equation (2) is inserted in equation (1), and once the transfer matrix has been transformed, this gives $$G_{\xi,k} = V_\xi c_k^{-1} \qquad (3)$$

The individual elements of the transfer matrix can thus be determined by calculating, for each location $\vec{x}_k$ at which the delta probe is positioned, the elements $G_{\xi,k}$ in accordance with equation (3), wherein $V_\xi$ are the real measured values transformed in the evaluation space which were acquired while the delta probe was located at the respective location $\vec{x}_k$.

Each matrix element $G_{\xi,k}$ is assigned an index value $\omega_\xi$, and thus also a transformed real measured value $V_\xi$ and a location $\vec{x}_k$ in the examination area. A matrix element $G_{\xi,k}$ of the transfer matrix is determined in accordance with equation (3) by positioning the delta probe at a location $\vec{x}_k$ which is assigned to the matrix element and by recording real measured values $V_t$ as in step 102. The real measured values $V_t$ are transformed as in step 103, and each transformed real measured value $V_\xi$ is assigned an index value $\omega_\xi$, wherein the assigned index value $\omega_\xi$ is the frequency of the transformed measured value $V_\xi$. The transformed real measured value $V_\xi$, which is assigned to the index value $\omega_\xi$, which is also assigned to the matrix element $G_{\xi,k}$, is then multiplied by the reciprocal value of the concentration of magnetic particles of the delta probe.

The transfer matrix G can also be determined in accordance with the equation $G_{t,k} = V_t c_k^{-1}$ if in other embodiments the recorded real measured values are not transformed in step 103.

If a transfer function for the apparatus 9 is known, for example on account of physical considerations, the transfer matrix can thus be formed by discretizing the transfer function.

If the transfer matrix has been determined for a specific path on which the first part-region 301 moves relative to and in the examination area, that is to say in this case for a specific temporally variable second magnetic field, this transfer matrix can be used for subsequent measurements and evaluations which use the same path, so that step 104 can then be omitted.

In step 105, an intermediate matrix A is formed in accordance with the following equation:

$$A = G^H G + \lambda H^H H \qquad (4)$$

Here, $G^H$ is the adjoint transfer matrix, $\lambda$ is a regularization parameter, H is a regularization matrix and $H^H$ is the adjoint regularization matrix.

The intermediate matrix A is formed in order to minimize the expression $$\|\vec{V} - G\vec{c}\|^2 + \lambda F(\vec{c}) \qquad (5)$$

by means of the subsequent steps 106 and 107. This expression is minimized for example when it assumes a minimum value which may or may not be equal to zero. Here, $F(\vec{c})$ is a regularization functional which is represented by the square of the norm of the regularization matrix, $F(\vec{c}) = \|H\vec{c}\|^2$.

Furthermore, $\vec{V}$ is a measured value vector which comprises as elements the transformed real measured values $V_\xi$, that is to say in this example of embodiment the frequency components of the Fourier-transformed measured values having the frequencies $\omega_\xi$. Moreover, $\vec{c}$ is a concentration vector which comprises as elements the concentrations $c_i$ at the locations $\vec{x}_i$. As explained above, the expression $\| \|$ denotes the norm.

When the regularization parameter $\lambda$ is equal to zero, by minimizing the expression $\|\vec{V} - G\vec{c}\|^2$ a spatial distribution of magnetic particles is determined in such a manner that a difference of the recorded real measured values $\vec{V}$ from fictitious measured values $G\vec{c}$, which have been calculated by applying the transfer function to the spatial distribution of magnetic particles, is minimized. Such a reconstruction makes it possible to determine reconstructed images of good quality with a calculation complexity which is lower than if the complete sum according to expression (5) were to be minimized.

An even better image quality can be obtained when a regularization parameter which is not equal to zero is selected. This is because, on account of the measured value noise, different measured values are recorded in different measurements for a given spatial distribution of magnetic particles, so that different reconstructed spatial distributions of magnetic particles may be obtained when minimizing the expression $\|\vec{V} - G\vec{c}\|^2$ for different measurements. If use is made of a suitable regularization parameter and of a suitable regularization matrix, the reconstruction can be influenced such that not just any of the various spatial distributions is reconstructed but rather one with a good image quality. The regularization parameter $\lambda$ in this case shows the extent of the influence of the regularization matrix H, that is to say of the regularization functional, on the determination of the spatial distribution of magnetic particles.

The regularization matrix H is defined in such a manner that a spatial distribution of magnetic particles with as good an image quality as possible is determined. To this end, use may be made of known regularization matrices which have been determined for example before the method according to the invention is carried out.

Regularization parameters $\lambda$ and regularization matrices H which lead to good image qualities can be determined for example by arranging a known test distribution of magnetic particles in the examination area and by measuring signals induced according to steps 101 to 107 and reconstructing the spatial distribution of magnetic particles. The spatial distribution of magnetic particles is reconstructed a number of times using different regularization parameters and regularization matrices, wherein, for each reconstructed distribution, a difference of the reconstructed distribution from the actual test distribution is calculated for example in accordance with the following equation:

$$\sum_i (c_i^w - c_i^r)^2 \tag{6}$$

Here, $c_i^w$ is the actual concentration of magnetic particles at the location $\vec{x}_i$, and $c_i^r$ is the reconstructed concentration at the same location. In order to apply the method according to the invention to an unknown spatial distribution of magnetic particles, use is then made of the combination of regularization parameter $\lambda$ and regularization matrix H for which the difference of the reconstructed distribution from the actual distribution is smallest.

The regularization parameter $\lambda$ preferably lies in the order of magnitude of $10^{-5}\lambda_0$ where $$\lambda_0 = \frac{Sp(G^H G)}{Sp(H^H H)} \tag{7}$$

wherein the expression $Sp(\ )$ describes the trace of a matrix. A regularization matrix H which leads to reconstructed images having a good image quality is for example a regularization matrix for which $H^H H = E$, wherein E is the unit matrix, that is to say the regularization matrix is unitary.

In step 106 the intermediate matrix A is inverted, and in step 107 the spatial distribution of magnetic particles is calculated in accordance with the following equation:

$$\vec{c} = A^{-1} G^H \vec{V} \tag{8}$$

According to equation (8), the real measured values transformed in the evaluation space are firstly represented as a measured value $\vec{V}$ and then multiplied by the transposed transfer matrix $G^H$ and by the inverse intermediate matrix $A^{-1}$. The resulting concentration vector $\vec{c}$ gives the reconstructed spatial distribution of magnetic particles in the examination area.

The spatial distribution of magnetic particles which is calculated in accordance with equation (8) minimizes expression (5) and thus leads to improved image qualities compared to the prior art. In other embodiments, use may be made according to the invention of other methods which determine a spatial distribution of magnetic particles for which expression (5) is minimized.

If it is desired to reconstruct the spatial distribution of magnetic particles a number of times using different regularization parameters and/or regularization matrices, for example in order to determine as described above a combination of regularization parameter and regularization matrix which leads to a high-quality image of the spatial distribution, preferably a singular value decomposition of the transfer matrix G is carried out. According to the known singular value decomposition, each matrix G can be represented by the following equation:

$$G = USB^H \tag{9}$$

wherein U and B are determined such that S is a diagonal matrix, that is to say for matrix elements $s_{i,k}$ the following applies: $s_{i,k} = 0$ for all $i \neq k$. The singular value decomposition and the determination of the matrices U, B and S are known, so that no further explanation thereof is given here. The superscript index H denotes an adjoint matrix.

Inserting equation (9) into equation (8) and taking account of equation (4) leads to $$\vec{c} = B(S^H S + \lambda B^H H^H H B)^{-1} B^H G^H \vec{V} \quad (10)$$

A calculation of the distribution of magnetic particles in the examination area in accordance with equation (10) has the advantage that, for different regularization parameters and regularization matrices, only the expression $(S^H S + \lambda B^H H^H H B)^{-1}$ has to be inverted. This expression can be more easily inverted than the intermediate matrix if the regularization matrices are selected such that the expression $B^H H^H H B$ comprises as few non-diagonal elements as possible which are not equal to zero. In one preferred embodiment, therefore, in order to determine the regularization matrices and the regularization parameters, use is made of regularization matrices for which the expression $B^H H^H H B$ comprises as few non-diagonal elements as possible which are not equal to zero.

In step 106, the intermediate matrix $A = G^H G + \lambda H^H H$ has to be inverted. If the regularization matrix is selected such that $H^H H = E$, the regularization matrix affects only the diagonal elements of the intermediate matrix, so that the regularization contribution does not make the inversion of the intermediate matrix more difficult. However, the inversion of the intermediate matrix by the expression $G^H G$ may be very complex in terms of calculation, particularly if $G^H G$ has many non-diagonal elements. In order to reduce this calculation complexity, the concentration vector $\vec{c}$ can be described by the following equation:

$$\vec{c} = G_1 \vec{q} \quad (11)$$

That is to say that the concentration vector $\vec{c}$ is developed in accordance with a new set of basic vectors which are the columns of a transformation matrix $G_1$, that is to say the concentration vector $\vec{c}$ is transformed from a space which is covered by the individual locations $\vec{x}_i$ in the examination area into a space which is covered by these basic vectors.

Here, the vector $\vec{q}$ describes a dependence distribution since the vector $\vec{q}$ is dependent on the spatial distribution $\vec{c}$ of magnetic particles in the examination area. If the transformation matrix is the same as the unit matrix, the dependence distribution is the same as the spatial distribution of magnetic particles.

When equation (11) is inserted into (1), the following is obtained:

$$\vec{V} = G G_1 \vec{q} = G_2 \vec{q} \text{ where } G_2 = G G_1 \quad (12)$$

The original transfer matrix has therefore been replaced by a transformed transfer matrix $G_2$. The intermediate matrix is now accordingly $A = G_2^H G_2 + \lambda H^H H$. Such a representation of the intermediate matrix A has the advantage that the transformation matrix $G_1$ can be defined in such a way that the inversion of the intermediate matrix A in step 106 is possible with a reduced calculation complexity, for example when the regularization matrix is the unit matrix, by defining the transformation matrix $G_1$ such that the matrix product $G_2^H G_2$ has as many non-diagonal elements as possible which are equal to zero, so that the matrix product can be easily inverted. This is the case in particular when the adjoint transfer matrix $G^H$ is used as the transformation matrix $G_1$.

In one embodiment according to the invention, which uses equation (12), firstly steps 101 to 104 are carried out, as described above, wherein the transfer matrix G determined in step 104 is a preliminary transfer matrix. In step 105, a transformation matrix $G_1$ is then determined such that the intermediate matrix $A = G_2^H G_2 + \lambda H^H H$ can be inverted in step 106 with a low calculation complexity. This may be achieved for example, when the regularization matrix is selected such that $H^H H = E$, by selecting a transformation matrix such that the product matrix $G G_1$ has as many non-diagonal elements as possible which are zero. In particular, the transformation matrix is selected such that the product matrix can be inverted with a lower calculation complexity then the preliminary matrix. Once the intermediate matrix has been inverted, firstly the vector $\vec{q}$ is determined in step 107 in accordance with the equation $\vec{q} = A^{-1} G_2^H \vec{V}$, whereupon the concentration of the magnetic particles in the examination area is calculated in accordance with equation (11).

Once the adjoint transfer matrix $G^H$ has been determined and the intermediate matrix has been inverted for a given transformation of the measured values in step 103 and a given movement of the first part-region 301 relative to and in the examination area, that is to say for a given, temporally variable second magnetic field, in subsequent measurements which in step 103 use the same transformation of the measured values and the same movement of the first part-region 301 relative to and in the examination area, following the transformation in step 103 the concentration distribution of magnetic particles in the examination area can be determined directly in accordance with equation (8) $\vec{c} = A^{-1} G^H \vec{V}$, that is to say the calculation-intensive steps 104 to 106 are then no longer necessary.

The regularization parameter and the regularization functional may be different for different applications. For example, they may have different values for an examination of a gastrointestinal tract, in which use may be made of a very large number of magnetic particles, than for an examination in which fewer magnetic particles are used.

In order to determine different regularization parameters and regularization functionals for different applications, the regularization functionals can be represented as regularization matrices, and different test distributions of magnetic particles which are adapted to the respective application are provided. As described above, in each case a combination of regularization parameter and regularization functional which leads to high-quality reconstructed images is determined for each of these test distributions. Then, for each application using the respective determined combination of regularization parameter and regularization functional, the inverse intermediate matrix and the transposed transfer matrix are determined and stored for example in the reconstruction unit. Once the intermediate matrix and the transposed transfer matrix have in each case been determined and stored for different applications, in a subsequent measurement the inverse intermediate matrix and transposed transfer matrix determined for the respective application can then be used directly to reconstruct an image of the examination area in accordance with equation (8).

A test distribution which can be used for examinations of the gastrointestinal tract is for example a test distribution which has a quantity and density of magnetic particles which corresponds to a quantity and density required to completely fill an examination area of the gastrointestinal tract. In other applications, use may be made of test distributions which have accordingly fewer magnetic particles.

The invention claimed is:

1. A method of determining a spatial distribution of magnetic particles (102) in an examination area, comprising the steps
   a) generating a first, temporally constant magnetic field with a spatial course of the magnetic field strength such that in the examination area there is a first part-region (301) having a relatively low magnetic field strength and a second part-region (302) having a relatively high magnetic field strength,
   b) changing the spatial position of the two part-regions (301, 302) in the examination area so that the magnetization of the particles (102) changes locally,
   c) recording real measured values which depend on the magnetization in the examination area, said magnetization being influenced by the change in position of the two part-regions (301, 302),
   d) reconstructing the spatial distribution ($\vec{c}$) of magnetic particles in the examination area from the real measured values, by means of the following steps:
   providing a transfer function which, applied to a dependence distribution which depends on a spatial distribution ($\vec{c}$) of magnetic particles, supplies fictitious measured values, and also providing a regularization parameter ($\lambda$) and a regularization functional (F) which can be applied to a dependence distribution which depends on a spatial distribution ($\vec{c}$) of magnetic particles,
   determining a dependence distribution which depends on a spatial distribution ($\vec{c}$) of magnetic particles, such that a sum which comprises as summands
   i) the difference of the real measured values ($\vec{V}$) from fictitious measured values which are determined by applying the transfer function to the dependence distribution, and
   ii) the product of the regularization parameter ($\lambda$) and of a regularization value which is determined by applying the regularization functional (F) to the dependence distribution, is minimized,
   e) determining using a processor, the spatial distribution ($\vec{c}$) of magnetic particles from the determined dependence distribution.

2. A method as claimed in claim 1, characterized in that the dependence distribution, which depends on a spatial distribution of magnetic particles, is the spatial distribution of magnetic particles itself.

3. A method as claimed in claim 2, characterized in that
   i) each real measured value ($V_t$) is assigned an index value (t),
   ii) the transfer function is represented by a transfer matrix (G) comprising matrix elements ($G_{t,k}$), wherein each matrix element ($G_{t,k}$) is assigned an index value (t) of a real measured value ($V_t$) and a location ($\vec{x}_k$) in the examination area, and
   iii) the transfer matrix (G) is provided by determining each matrix element ($G_{t,k}$) of the transfer matrix (G) by means of the following steps:
   positioning a delta probe of magnetic particles at the location ($\vec{x}_k$) which is assigned to the respective matrix element ($G_{t,k}$),
   carrying out steps a) to c),
   assigning the index values (t) to the real measured values ($V_t$),
   forming the product from the real measured value ($V_t$) which is assigned to the index value (t) which is assigned to the respective matrix element ($G_{t,k}$) and from the reciprocal value of the concentration ($c_k$) of magnetic particles of the delta probe, wherein the product is the matrix element ($G_{t,k}$).

4. A method as claimed in claim 1, characterized in that providing the regularization parameter ($\lambda$) and the regularization functional (F) comprises the following steps:
   i) providing a spatial test distribution of magnetic particles in the examination area,
   ii) carrying out steps a) to d), wherein different combinations of regularization parameter and regularization functional are provided in step d) so that in each case a spatial distribution of magnetic particles is reconstructed for each of these combinations,
   iii) determining in each case a difference of the spatial test distribution of magnetic particles from the spatial distribution of magnetic particles calculated for the respective combination,
   iv) providing that combination of regularization parameter and regularization functional for which the difference determined in step iii) is smallest.

5. A method as claimed in claim 4, characterized in that the transfer function is represented as the transfer matrix (G), to which a singular value decomposition is applied so that the transfer matrix is decomposed into a first matrix (U), a diagonal matrix (S) and a second matrix ($B^H$), wherein, instead of the transfer matrix (G), the same first matrix (U), the same diagonal matrix (S) and the same second matrix ($B^H$) are used for each combination of regularization parameter ($\lambda$) and regularization functional (F) for reconstructing the spatial distribution of magnetic particles.

6. A method as claimed in claim 1, characterized in that the regularization parameter ($\lambda$) is equal to zero.

7. A method as claimed in claim 1, characterized in that the real measured values ($V_t$) are transformed into transformed real measured values ($V_\xi$) prior to the reconstruction, in particular by means of a Fourier transformation, in such a manner that the number of transformed real measured values ($V_\xi$) is smaller than the number of non-transformed real measured values ($V_t$) and/or in such a manner that a transfer function can be provided which is easier to invert than a transfer function which would be provided if the real measured values were not transformed, and in that the transformed real measured values ($V_\xi$) are used in the reconstruction in step d).

8. A method as claimed in claim 7, characterized in that
   i) each transformed real measured value ($V_\xi$) is assigned an index value ($\omega_\xi$),
   ii) the transfer function is represented by a transfer matrix (G) comprising matrix elements ($G_{\xi,k}$), wherein each matrix element ($G_{\xi,k}$) is assigned an index value ($\omega_\xi$) of a transformed real measured value ($V_\xi$) and a location ($\vec{x}_k$) in the examination area, and iii) the transfer matrix (G) is provided by determining each matrix element ($G_{\xi,k}$) of the transfer matrix (G) by means of the following steps:

positioning a delta probe of magnetic particles at the location ($\vec{x}_k$) which is assigned to the respective matrix element ($G_{\xi,k}$), carrying out steps a) to c), transforming the real measured values into transformed real measured values ($V_\xi$), assigning the index values ($\omega\xi$) to the transformed real measured values ($V_\xi$), forming the product from the transformed real measured value ($V_\xi$) which is assigned to the index value ($\omega_\xi$) which is assigned to the respective matrix element ($G_{\xi,k}$) and from the reciprocal value of the concentration ($c_k$) of magnetic particles of the delta probe, wherein the product is the matrix element ($G_{\xi,k}$).

9. A method as claimed in claim 1, characterized in that the regularization functional (F) applied to a dependence distribution can be represented by the square of the norm of a dependence distribution vector, which describes the dependence distribution, multiplied by a regularization matrix (H), in that the transfer function can be represented by a transfer matrix (G), and in that determining the dependence distribution in step d) comprises the following steps:

determining an intermediate matrix (A) as the sum of i) the product of the adjoint transfer matrix ($G^H$) with the transfer matrix (G) and ii) the product of the regularization parameter ($\lambda$) with the product of the adjoint regularization matrix ($H^H$) with the regularization matrix (H), inverting the intermediate matrix (A) and forming the matrix product from the inverted intermediate matrix ($A^{-1}$) and the adjoint transfer matrix ($G^H$), determining the dependence distribution vector by multiplying the formed matrix product from the inverted intermediate matrix ($A^{-1}$) and the adjoint transfer matrix ($G^H$) by a measured value vector ($\vec{V}$) which comprises values dependent on the real measured values and in particular the real measured values themselves.

10. A method as claimed in claim 1, characterized in that step d) comprises the following steps:

providing a preliminary transfer matrix (G) which, applied to a given spatial distribution ($\vec{c}$) of magnetic particles, supplies fictitious measured values, providing a transformation matrix ($G_1$) which, applied to a dependence distribution ($\vec{q}$), supplies a spatial distribution ($\vec{c}$) of magnetic particles and which is adapted such that the product of the preliminary transfer matrix (G) with the transformation matrix ($G_1$) can be inverted more easily than the preliminary transfer matrix (G), providing a transfer matrix ($G_2$) as the transfer function, wherein a product matrix ($GG_1$) is formed by multiplying the preliminary transfer matrix (G) with the transformation matrix ($G_1$) and wherein the product matrix ($GG_1$) is provided as the transfer matrix ($G_2$), determining a dependence distribution ($\vec{q}$) such that a sum which comprises as summands i) the difference of the real measured values from fictitious measured values which are determined by applying the transfer matrix ($G_2$) to the dependence distribution ($\vec{q}$), and ii) the product of the regularization parameter ($\lambda$) and of a regularization value which is determined by applying the regularization functional ($F(\vec{q})$) to the dependence distribution ($\vec{q}$), is minimized, determining the spatial distribution ($\vec{c}$) of magnetic particles by applying the transformation matrix ($G_1$) to the dependence distribution ($\vec{q}$).

11. A method as claimed in claim 10, characterized in that i) each real measured value ($V_t$) is assigned an index value (t), ii) the preliminary transfer matrix (G) comprises matrix elements ($G_{t,k}$), wherein each matrix element ($G_{t,k}$) is assigned an index value (t) of a real measured value ($V_t$) and a location ($\vec{x}_k$) in the examination area, and iii) each matrix element ($G_{t,k}$) of the preliminary transfer matrix (G) is determined by means of the following steps:

positioning a delta probe of magnetic particles at the location ($\vec{x}_k$) which is assigned to the respective matrix element ($G_{t,k}$), carrying out steps a) to c), assigning the index values (t) to the real measured values ($V_t$), forming the product from the real measured value ($V_t$) which is assigned to the index value (t) which is assigned to the respective matrix element ($G_{t,k}$) and from the reciprocal value of the concentration ($C_k$) of magnetic particles of the delta probe, wherein the product is the matrix element ($G_{t,k}$).

12. An apparatus for carrying out the method as claimed in claim 1, comprising at least one first magnetic means (3a, 3b) for generating a first, temporally constant magnetic field with a spatial course of the magnetic field strength such that in the examination area there is a first part-region (301) having a relatively low magnetic field strength and a second part-region (302) having a relatively high magnetic field strength, means, in particular at least one second magnetic means (4a, 4b, 5a, 5b, 6a, 6b) for changing the spatial position of the two part-regions (301, 302) in the examination area so that the magnetization of the particles changes locally, at least one recording means (7) for recording real measured values which depend on the magnetization in the examination area, said magnetization being influenced by the change in spatial position of the two part-regions (301, 302), at least one reconstruction means (74) for reconstructing the spatial distribution ($\vec{c}$) of magnetic particles in the examination area from the real measured values, a control unit (10) for controlling the at least one first magnetic means (3a, 3b), the means (4a, 4b, 5a, 5b, 6a, 6b) for changing the spatial position of the two part-regions, the at least one recording means (7) and the at least one reconstruction means (74) in accordance with the steps of claim 1.

13. A computer program for a control unit (10) for controlling the at least one first magnetic means (3a, 3b), the means (4a, 4b, 5a, 5b, 6a, 6b) for changing the spatial position of the two part-regions, the at least one recording means (7) and the at least one reconstruction means (74) of an apparatus as claimed in claim 12 for carrying out the method of determining a spatial distribution of magnetic particles (102) in an examination area, comprising the steps     a) generating a first, temporally constant magnetic field with a spatial course of the magnetic field strength such that in the examination area there is a first part-region (301) having a relatively low magnetic field strength and a second part-region (302) having a relatively high magnetic field strength,     b) changing the spatial position of the two part-regions (301, 302) in the examination area so that the magnetization of the particles (102) changes locally,     c) recording real measured values which depend on the magnetization in the examination area, said magnetization being influenced by the change in position of the two part-regions (301, 302),     d) reconstructing, the spatial distribution ($\vec{c}$) of magnectic particles in the examination area from the real measured values, by means of the following steps:

providing a transfer function which, applied to a dependence distribution which depends on a spatial distribution ($\vec{c}$) of magnetic particles, supplies fictitious measured values, and also providing a regularization parameter ($\lambda$) and a regularization functional (F) which can be applied to a dependence distribution which depends on a spatial distribution ($\vec{c}$) of magnetic particles,     determining a dependence distribution which depends on a spatial distribution ($\vec{c}$) of magnetic particles, such that a sum which comprises as summands     i) the difference of the real measured values ($\vec{V}$) from fictitious measured values which are determined by applying the transfer function to the dependence distribution, and     ii) the product of the regularization parameter ($\lambda$) and of a regularizatlon value which is determined by applying the regularization functional (F) to the dependence distribution, is minimized,     e) determining the spatial distribution ($\vec{c}$) of magnetic particles from the determined dependence distribution.

\* \* \* \* \*